United States Patent [19]

Kleinknecht

[11] 4,188,123
[45] Feb. 12, 1980

[54] OPTICALLY MEASURING THE CARRIER CONCENTRATION IN A SEMICONDUCTOR

[75] Inventor: Hans P. Kleinknecht, Bergdietikon, Switzerland

[73] Assignee: RCA Corporation, New York, N.Y.

[21] Appl. No.: 938,246

[22] Filed: Aug. 30, 1978

[51] Int. Cl.² .................................. G01N 21/22
[52] U.S. Cl. ................................ 356/354; 356/128
[58] Field of Search ................ 356/128, 354, 445; 350/162 R; 250/550

[56] References Cited

U.S. PATENT DOCUMENTS

| 3,988,564 | 10/1976 | Garvin et al. | 219/121 EM |
|---|---|---|---|
| 4,039,370 | 8/1977 | Kleinknecht | 156/626 |

OTHER PUBLICATIONS

Rassudova et al., "Precision Diffraction Grating for Metrologic Purposes"; *Optics and Spectroscopy*, Aug. 1961, pp. 136–137.
Vasil'eva et al., "Measurement of the Selective Growth and Etching Rates of GaAs"; *Inorganic Materials*, vol. 12, Feb. 1976, pp. 162–164.

*Primary Examiner*—John K. Corbin
*Assistant Examiner*—R. A. Rosenberger
*Attorney, Agent, or Firm*—H. Christoffersen; D. S. Cohen; T. H. Magee

[57] ABSTRACT

A method of optically measuring the concentration of carriers in a doped region of a semiconductor wafer includes the step of selectively introducing conductivity modifiers into both the wafer and a test substrate simultaneously to form respectively the doped region in the wafer and a diffraction grating pattern in the substrate including periodically-spaced doped strips. The diffraction grating pattern is exposed to a beam of monochromatic light, and the intensity of one of the diffracted beams is measured, whereby the magnitude thereof is a measure of the carrier concentration in the doped region.

8 Claims, 1 Drawing Figure

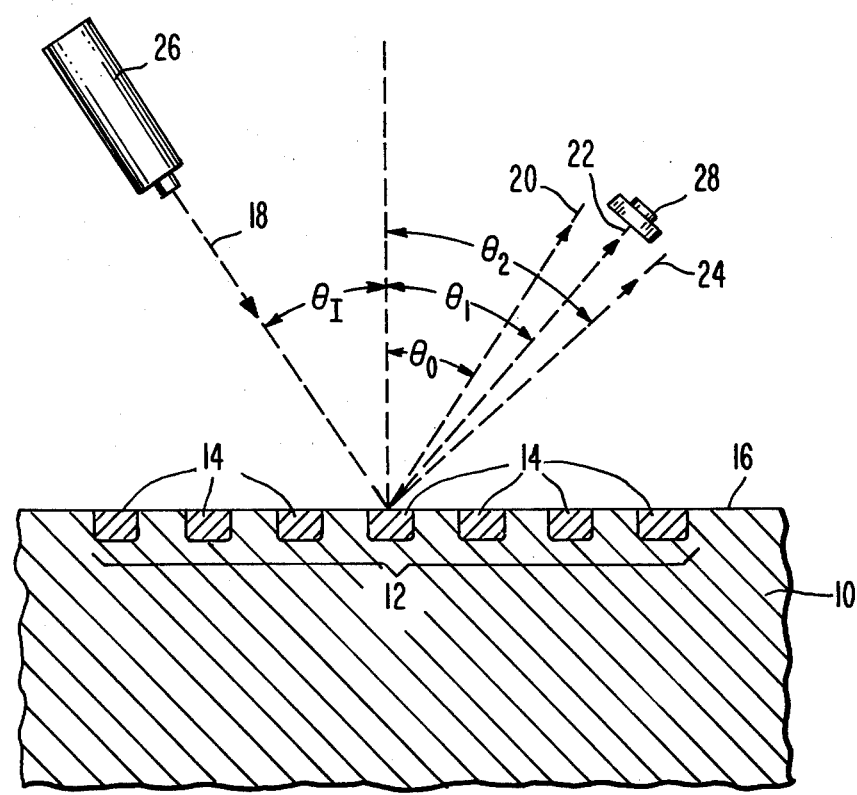

OPTICALLY MEASURING THE CARRIER CONCENTRATION IN A SEMICONDUCTOR

This invention relates to a method of optically measuring the carrier concentration in a semiconductor wafer.

In manufacturing integrated circuit (IC) devices, one of the more important parameters which is closely watched during semiconductor device fabrication is the concentration of current carriers, i.e., the number of free electrons and holes, in the semiconductor wafer. It is routinely monitored in IC manufacturing by taking sheet resistance measurements uutilizing a four-point probe. This technique requires a test area on the wafer of several millimeters on a side, and it tends to leave small marks on the surface from the probe contact points. For these reasons, one can not do these measurements on product wafers, but has to include in each production lot a number of control wafers for this purpose.

Another disadvantage of the sheet resistance measurement is the fact that it contains not the carrier concentration alone but the product of carrier concentration and mobility averaged through the whole wafer. Although the use of ion implantation for the introduction of conductivity modifiers gives the possibility to know exactly the number of dopant atoms per square centimeter introduced into the wafer, there remains however, the uncertainty about what percentage of dopant atoms is located on substitutional lattice sites, where it produces free carriers. And there remains also the question about the depth distribution of the conuctivity modifiers beneath the surface of the wafer.

The present invention provides an optical technique for measuring carrier concentration on the surface of a semiconductor wafer. Since this technique requires no contacts and no touching, it can be used directly on product wafers, thereby eliminating the need for four-point-probe control wafers. The proposed method provides a measurement of the carrier concentration alone, regardless of the mobility and the percentage of dopant atoms located at interstitial sites. It measures primarily the carrier concentration on the surface, but it also can be used to give a measurement of the concentration gradient into the depth of the doped wafer.

IN THE DRAWING

The FIGURE is a cross-sectional view illustrating diagrammatically a beam of light striking a diffraction grating pattern and being diffracted into diffracted beams of the zero, first and second orders.

The present novel invention utilizes the influence of free electrons and holes on the refractive index of a semiconductor material. The refractive index for a material is a ratio of the sine of the angle of incidence to the sine of the angle of refraction when a light ray passing through a vacuum (or for practical purposes air) strikes the surface of the material and is divided into a reflective ray and a refractive ray. The effectiveness of the semiconductor surface in reflecting light, i.e., its reflectivity, is thus influenced by the index of refraction for the semiconductor material and may be monitored by measuring the intensity of the reflected ray. Since this effect is very small in principle, my invention uses the enhancing effect of a diffraction grating. In other words, a periodic doping distribution is produced along the surface of the semiconductor material. This is accomplished in the manufacturing process by adding grating-like test patterns to the doping mask which controls the pre-diffusion deposition or ion implantation of the particular doping step.

Referring to the drawing, there is shown a substrate 10 of semiconductor material which may be part of a large silicon wafer having integrated circuit devices (not shown) disposed therein. In fabricating such devices, conductivity modifiers are selectively introduced into the wafer through openings in a masking layer disposed adjacent a surface of the wafer to form doped regions therein. In order to measure the concentration of carriers in one of the doped regions of such a device, I disclose a method comprising selectively introducing conductivity modifiers into both that part of the wafer which is used for making devices and into a test substrate 10, preferably a test area on the same wafer, simultaneously to form respectively the doped region in the wafer and a diffraction grating pattern 12 in the substrate 10 including periodically-spaced doped strips 14 adjacent a surface 16 of the substrate 10. The test substrate 10 has a background concentration similar to that of the device area of the wafer and may conveniently comprise a knock-out section of the silicon wafer, i.e., an unused section in the middle of the wafer, or may even fit onto the side of each step and repeated circuit pattern. The grating pattern 12 is preferably formed by photolithographically masking the surface 16 of the substrate 10 and then ion implanting or diffusing conductivity modifiers into the substrate 10 through rectangular openings in the masking layer (not shown) having the same width and periodicity as the desired periodically-spaced strips 14. Several patterns were fabricated by implanting boron into N type substrates and phosphorus into P type substrates with an implantation depth of 0.12 micrometers and peak doping concentrations of $10^{17}$, $10^{18}$, $10^{19}$ and $10^{20}$ cm$^{-3}$. In the present embodiment, the width of the strips 14 is approximately 2 micrometers and the periodicity of the diffraction grating pattern 12 is about 5 micrometers.

The diffraction grating pattern 12 is exposed to a beam 18 of monochromatic light, such as a laser beam. The diffraction grating pattern 12 functions as a reflection phase grating, diffracting the beam 18 of monochromatic light into a diffraction pattern including a zero order beam 20, a first order beam 22 and a second order beam 24. In one experimental embodiment, the light beam 18 had a diameter of approximately 2 millimeters, striking the diffraction grating pattern 12 uniformly so that all portions thereof were uniformly exposed to the incident light beam 18. The use of a He-Ne gas laser 26 having a wavelength, λ, equal to 0.6328 micrometers is preferred due to the fact that it is relatively cheap, reliable, and convenient to use. The angular positions of the various diffracted orders depend only on the grating period, d, and on the wavelength, λ. The diffraction angle, θ, for a diffraction grating, is a function of λ and d according to the following expression:

$$\mathrm{Sin}\ \theta = \mathrm{Sin}\ \theta_I + m\lambda/d$$

where $\theta_I$ is the angle of the incident light beam 18, d is the periodicity, m is the diffraction order. Referring to the drawing, $\theta_1$ and $\theta_2$ are the diffraction angles for the first and second order beams 22 and 24, respectively.

The intensity of one of the diffracted beams, preferably the first order beam 22 because it is strongest, is now measured by utilizing a photodetector 28 placed at the appropriate diffraction angle $\theta_1$ to receive the first order beam 22. In the present embodiment, the photodetector 28 comprises a silicon PIN diode (reverse biased at 10 volts). A part of the light beam 18 which strikes the diffraction grating pattern 12 is reflected from the doped surface 16 while other parts (not shown) of the beam 18 enter the doped strips 14 and then go through one or more internal reflections before immerging therefrom. The measured intensity of the diffracted beams is a result of the interference of these partial beams.

The intensity of the first order beam 22 is a measure of the carrier concentration in the doped strips 14 since the index of refraction and, through that, the reflectivity are affected by the number of free holes and electrons in the doped strips 14. The strips 14 are doped higher than the bulk of the substrate 10 and correspondingly have a lower refractive index and lower reflectivity. In particular, the intensity of the first order beam 22 is proportional to the square of the carrier concentration in the doped strips 14. This allows for the determination of the carrier concentration in the doped strips 14 by measuring the light intensity of the first order diffracted beam 22. The carrier concentration measured in this way is sampled from a depth of about $\lambda/2\pi$ n, where $\lambda$ is the wavelength of the light beam and n is the refractive index of the substrate 10. In the present example, the light beam 18 used is a red He-Ne laser beam ($\lambda = 0.6328$ micrometers) and the substrate 10 is silicon (n≈3.4), so the carrier concentration is sampled from a depth of about 0.03 micrometers.

Using the above, one is able to sample the carrier concentration at different depths in the doped strips 14 of the substrate 10 by successively exposing the diffraction grating pattern 12 to a plurality of beams of monochromatic light having different wavelengths. For example, using an infrared He-Ne laser ($\lambda = 3.39$ micrometers) and a $CO_2$ laser ($\lambda = 10.6$ micrometers), the carrier concentration in the doped strips 14 is sampled, respectively, at depths of about 0.16 micrometers and about 0.47 micrometers. Hence, measurements with various wavelengths give the possibility to obtain a depth profile.

If the area of the diffraction pattern 12 is small, there may be a problem with the overlap of the desired first order beam 22 by the strong zero order beam 20 which is nearly independent of the doping concentration. This situation can be improved dramatically if the light is polarized parallel to the plane of incidence and strikes the diffraction grating pattern 12 uniformly at an angle of incidence $\theta_I$ = Brewster's angle, defined by the relationship TAN $\theta_I = n$. For the present example where the substrate is silicon (n≈3.4), Brewster's angle would be at $\theta_I = 73.6°$. Under this condition the regular reflection can be significantly suppressed. It is then only limited to a spurious reflection due to imperfect polarization and to divergence of the light beam 18. The diffraction pattern due to the periodic carrier concentration now shows up more clearly.

In order to further substantiate the utility of the present method, Table I provides some practical grating pattern sizes for typical carrier concentrations. The top row of Table I gives the carrier concentration, while the second and third rows show the fractional changes of refractive index and reflectivity, respectively. In the fourth row, using a wavelength, $\lambda$, equal to 3.39 micrometers and a grating periodicity of 5 micrometers, I have calculated the diameter of the grating pattern 12 necessary to obtain a signal-to-background ratio of 10 for normal incidence. In the fifth row I have done the same for Brewster's angle condition assuming a polarization ratio of 1:500,000 and a laser beam divergence of 1 milliradian. These values show that carrier concentrations of $10^{17}$ cm$^{-3}$ can be measured with the Brewster's angle arrangement using practical size diffraction grating patterns.

TABLE 1

| CARRIER CONCENTRATION | $10^{17}$cm$^{-3}$ | $10^{18}$cm$^{-3}$ | $10^{19}$cm$^{-3}$ | $10^{20}$cm$^{-3}$ |
|---|---|---|---|---|
| FRACTIONAL DECREASE OF REFRACTIVE INDEX | $1.5 \cdot 10^{-4}$ | $1.5 \cdot 10^{-3}$ | $1.5 \cdot 10^{-2}$ | $1.5 \cdot 10^{-1}$ |
| FRACTIONAL DECREASE OF REFLECTIVITY | $2 \cdot 10^{-4}$ | $2 \cdot 10^{-3}$ | $2 \cdot 10^{-2}$ | $2 \cdot 10^{-1}$ |
| DIAMETER OF GRATING AREA FOR NORMAL INCIDENCE | — | 16 mm | 1.6 mm | 160 $\mu$ |
| DIAMETER OF GRATING AREA FOR BREWSTER'S INCIDENCE | 2 mm | 200 $\mu$ | 20 $\mu$ | — |

The present novel technique provides a method of measuring the concentration of carriers near the surface of a semiconductor substrate by their influence on the reflectivity. The use of various wavelengths from 0.6328 to 10 micrometers yields information about the depth profile of the doping between 0.03 and 0.5 micrometers from the surface. In contrast to sheet resistivity measurements, these data are independent of mobility and measure the concentration per cubic centimeter and not per square centimeter. By interfacing a microprocessor to such a method, this technique allows for rapid and objective testing of carrier concentrations in integrated circuit patterns, resulting in considerable savings in the man-hours needed for taking four-point sheet resistance measurements.

What is claimed is:

1. A method of optically measuring the concentration of carriers in a doped region adjacent a surface of a semiconductor wafer comprising the steps of:
   selectively introducing conductivity modifiers into both said wafer and a test substrate simultaneously to form respectively said doped region in said wafer and a diffraction grating pattern in said substrate including periodically-spaced doped strips adjacent a surface of said substrate,
   exposing said diffraction grating pattern to a beam of monochromatic light, whereby said diffraction grating pattern functions as a reflection phase grating, diffracting said beam of monochromatic light into diffracted beams of various orders, and
   measuring the intensity of one of said diffracted beams, whereby the magnitude thereof is a measure of the carrier concentration in said doped region.

2. A method as recited in claim 1 further comprising the steps of successively exposing said diffraction grating pattern to a plurality of beams of monochromatic light having different wavelengths, whereby the intensity measurements are a measure of the carrier concentration at different depths in said region.

3. A method as recited in claim 1 wherein said beam of monochromatic light is polarized parallel to the plane of incidence and strikes said diffraction grating pattern uniformly at an angle of incidence $\theta_I$ equal to Brewster's angle, defined by the relationship TAN $\theta_I = n$, where n is the refractive index of said semiconductor wafer.

4. A method as recited in claim 3 wherein said beam of monochromatic light is a laser beam.

5. A method as recited in claim 1 wherein said measuring step is performed by utilizing a photodetector placed at an angular position to receive the first order beam.

6. A method as recited in claim 5 wherein said photodetector is a silicon PIN diode.

7. A method as recited in claim 1 wherein said test substrate comprises a knock-out section of said wafer.

8. A method as recited in claim 7 wherein said wafer is silicon, wherein the width of said periodically-spaced strips is about 2 micrometers and wherein the periodicity of said diffraction grating pattern is about 5 micrometers.

* * * * *